United States Patent
Takeuchi et al.

(10) Patent No.: US 6,319,340 B1
(45) Date of Patent: Nov. 20, 2001

(54) TI-V-Al BASED SUPERELASTICITY ALLOY AND PROCESS FOR PREPARATION THEREOF

(76) Inventors: Mikio Takeuchi; Hiroyuki Tada, both of c/o Horikawa Inc., 6-8, Kawasari-cho, Sabae-shi, Fukui 916-0088 (JP); Kanryu Inoue, 5414-154th Ave., SE., Bellevue, WA (US) 98006

( * ) Notice: Subject to any disclaimer, the term of this patent is extended or adjusted under 35 U.S.C. 154(b) by 0 days.

(21) Appl. No.: 09/424,206
(22) PCT Filed: Mar. 19, 1999
(86) PCT No.: PCT/JP99/01378
§ 371 Date: Nov. 22, 1999
§ 102(e) Date: Nov. 22, 1999
(87) PCT Pub. No.: WO99/49091
PCT Pub. Date: Sep. 30, 1999

(30) Foreign Application Priority Data

Mar. 23, 1998 (JP) .................................................. 10-074016

(51) Int. Cl.[7] .................................................. C22C 14/00
(52) U.S. Cl. ........................... 148/421; 148/669; 420/420
(58) Field of Search ............................. 148/421, 669, 148/670, 671; 420/420

(56) References Cited

U.S. PATENT DOCUMENTS 4,134,758 * 1/1979 Nagai et al. .
4,600,449 * 7/1986 White et al. .......................... 148/407

FOREIGN PATENT DOCUMENTS

| 61-250138 | 11/1986 | (JP) . |
| 63-250445 * | 10/1988 | (JP) . |
| 63-250446 * | 10/1988 | (JP) . |
| 3-115550 * | 5/1991 | (JP) . |
| 10-81928 | 3/1998 | (JP) . |
| 10-81298 * | 3/1998 | (JP) . |

OTHER PUBLICATIONS

Shika Zairyou Kikai, vol. 5, No. 1, Jan. 25, 1986, (25.01.86), pp. 155–161.

Nippon Kinzoku Gakkai Symposium Kouen Yokou Ippan Kouen Gaiyou, vol. 97th, Sep. 13, 1985 (13.09.85), p. 121.

* cited by examiner

*Primary Examiner*—John Sheehan
(74) *Attorney, Agent, or Firm*—Larson & Taylor PLC

(57) ABSTRACT

A Ti—V—Al based superelastic alloy wherein the proportions of Ti, Al and V, based on the total weight of the three components, fall within the range defined by the lines joining the following points of A, B, C and D shown in the ternary composition diagram of accompanying FIG. 1:
A: 79.8% Ti, 17.5% V, 2.7% Al,
B: 76.8% Ti, 20.5% V, 2.7% Al,
C: 73.8% Ti, 20.5% V, 5.7% Al,
D: 76.8% Ti, 17.5% V, 5.7% Al.

5 Claims, 5 Drawing Sheets

TI-V-Al BASED SUPERELASTICITY ALLOY AND PROCESS FOR PREPARATION THEREOF

TECHNICAL FIELD OF THE INVENTION

The present invention relates to a superelastic alloy not containing nickel, more specifically to a Ti—V—Al based superelastic alloy which has high corrosion resistance and is lightweight and to processes for its preparation.

BACKGROUND ART

Known as functional alloys exhibiting superelasticity are Au—Cd alloys, Cu—Zn—Al alloys, Cu—Al—Ni alloys, Ni—Ti alloys and the like.

Of those functional alloys, Ni—Ti alloys have attracted attention, for example, as orthopedic implant materials due to their superiority in corrosion resistance. However, Ni—Ti alloys, in contact with body tissue, are known to cause inflammation to the contact part. Moreover, the effect of dissolved Ni ions on body tissue (e.g., carcinogenesis) has not been fully studied and safety has not yet been confirmed. Therefore, Ni—Ti alloys cannot be implanted into the body as they are (i.e., without coating). Furthermore, since nickel in Ni-containing articles such as pierced earrings, wristwatch bands or the like, which are used in contact with the skin, dissolves in sweat and induces allergies, it might be highly dangerous to use Ni—Ti alloys as implant materials.

Known as Ni-free shape memory alloys are Ti alloys (U.S. Pat. No. 4,412,872), etc. However, there are no known Ni-free superelastic alloys that are easy to use as structural materials for industrial use and have high corrosion resistance and improved workability.

OBJECT OF THE INVENTION

A primary object of the present invention is to provide a Ni-free superelastic alloy that is easy to use as a structural material for industrial use and has high corrosion resistance and improved workability.

DISCLOSURE OF THE INVENTION

In view of the state of the prior art, the present inventors carried out extensive research and found that Ti—V—Al based alloys having a specific composition range exhibit superelasticity over a broad range of temperatures and have various excellent properties such as high corrosion resistance and improved workability.

The present invention provides the following Ti—V—Al based alloy and processes for its preparation.

1. A Ti—V—Al based superelastic alloy wherein the proportions of Ti, Al and V, based on the total weight of the three components, fall within the range defined by the lines joining the following points of A, B, C and D shown in the ternary composition diagram of accompanying FIG. 1:
A: 79.8% Ti, 17.5% V, 2.7% Al,
B: 76.8% Ti, 20.5% V, 2.7% Al,
C: 73.8% Ti, 20.5% V, 5.7% Al,
D: 76.8% Ti, 17.5% V, 5.7% Al.

2. A process for preparing a Ti—V—Al based superelastic alloy, which comprises melt-forming an alloy wherein the proportions of Ti, Al and V, based on the total weight of the three components, fall within the range defined by the lines joining the following points of A, B. C and D shown in the ternary composition diagram of accompanying FIG. 1, followed by heat treatment at 800° C. to 1200° C. and quenching:
A: 79.8% Ti, 17.5% V, 2.7% Al,
B: 76.8% Ti, 20.5% V, 2.7% Al,
C: 73.8% Ti, 20.5% V, 5.7% Al,
D: 76.8% Ti, 17.5% V, 5.7% Al.

3. A process for preparing a Ti—V—Al based superelastic alloy, which comprises melt-forming an alloy wherein the proportions of Ti, Al and V, based on the total weight of the three components, fall within the range defined by the lines joining the following points of A, B, C and D shown in the ternary composition diagram of accompanying FIG. 1, followed by heat treatment at 800° C. to 1200° C. and quenching and then aging the alloy at temperatures no higher than 200° C.:
A: 79.8% Ti, 17.5% V, 2.7% Al,
B: 76.8% Ti, 20.5% V, 2.7% Al,
C: 73.8% Ti, 20.5% V, 5.7% Al,
D: 76.8% Ti, 17.5% V, 5.7% Al.

The superelastic alloy of the present invention is prepared by melt-forming a basic alloy according to a conventional method, the proportions of Ti, Al and V in the alloy being selected from the range defined by the lines joining the points of A (79.8% Ti, 17.5% V, 2.7% Al), B (76.8% Ti, 20.5% V, 2.7% Al), C (73.8% Ti, 20.5% V, 5.7% Al) and D (76.8% Ti, 17.5% V, 5.7% Al) shown in the ternary composition diagram of accompanying FIG. 1, followed by subjecting the basic alloy to heat treatment at 800° C. to 1200° C. and quenching.

The superelastic alloy according to the present invention may contain unavoidable impurities as long as the properties of the alloy are not impaired.

According to the present invention, $\beta$ phase formed by heat treatment is prevented from transforming to $\alpha$ phase, $\alpha+\beta$ phase, $\omega$ phase or the like by quenching the Ti—V—Al alloy from the heat treatment temperature. Therefore, the alloy exhibits satisfactory superelasticity over a broad range of temperatures from liquid nitrogen temperature to about 80° C.

There is no specific limitation on the alloy-quenching method and quenching rate. A typical alloy-quenching method comprises immersing an ally ingot in a sufficient amount of water to quench the ingot from the heat treatment temperature. For example, when 30 g of a button-shaped alloy ingot obtained according to an embodiment of the present invention is immersed in about 20° C. water, the quenching rate is at least about 300° C./sec.

Especially, when the thus obtained Ti—V—Al based superelastic alloy of the present invention is further aged within the temperature range where $\omega$ phase does not form (about 200° C. to about –30° C.), the alloy exhibits superelasticity throughout a broad range of temperatures from about 80° C. to about liquid nitrogen temperature (–196° C.).

To improve cold workability, it is preferable for the superelastic alloy of the present invention to have a Ti—Al—V composition selected from the range defined by the lines joining the points of A (79.8% Ti, 17.5% V, 2.7% Al), B (76.8% Ti, 20.5% V, 2.7% Al), E (75.0% Ti, 20.5% V, 4.5% Al) and F (78.0% Ti, 17.5% V, 4.5% Al) shown in the ternary Ti—Al—V composition diagram of FIG. 1.

To reduce costs without substantially impairing the properties of the alloy, it is preferable for the superelastic alloy of the present invention to have a Ti—Al—V composition selected from the range defined by the lines joining the points of A (79.8% Ti, 17.5% V, 2.7% Al), G (77.8% Ti, 19.5% V, 2.7% Al), H (74.8% Ti, 19.5% V, 5.7% Al) and D (76.8% Ti, 17.5% V, 5.7% Al).

To improve cold workability and reduce costs, it is preferable for the superelastic alloy of the present invention to have a Ti—Al—V composition selected from the range defined by the lines joining the points of A (79.8% Ti, 17.5% V, 2.7% Al), G (77.8% Ti, 19.5% V, 2.7% Al), I (76.0% Ti, 19.5% V, 4.5% Al) and F (78.0% Ti, 17.5% V, 4.5% Al).

The Ti—V—Al based superelastic alloy of the present invention has high corrosion resistance similarly to Ti—V—Al alloys that do not have superelastisity but are useful as aircraft materials.

As compared with Ti—Ni based superelastic alloys, the superelastic alloy of the invention is lightweight.

Further, since the superelastic alloy of the present invention is comparatively low in hardness and has improved press workability, end cracking and warping associated with cold working are less likely to occur.

Still further, like known Ti—V—Al based alloys utilized as implant materials, the superelastic alloy of the present invention is highly safe for use within the body and does not cause inflammation to body tissues such as the skin, even when in contact with the body tissue for a long period of time.

In the substantially ternary superelastic alloy according to the present invention, aging can be facilitated by either adding at least one of elements such as Cr, Nb, Mo and the like to the alloy, or replacing a part of Al present in the alloy with Si and/or Ge (a quaternary or higher alloy). In more detail, if the quaternary alloy is aged under the conditions where the martensitic transformation occurs while austenite as the parent phase is dominant, the alloy acquires superelasticity and has the same functional properties as the ternary alloy of the present invention.

Of conventional Ti—V—Al alloys and other Ti alloys, there are no known functional alloys that acquire superelasticity upon low temperature aging treatment. Of conventional Ti—V—Al alloys, there are no known functional alloys that exhibit superelasticity throughout a broad range of temperatures from about 80° C. to about liquid nitrogen temperature. Therefore, the Ti—V—Al alloy of the present invention is a material that is highly useful and exhibits novel functions.

EFFECTS OF THE INVENTION

According to the invention, the following remarkable effects are achieved.

(1) The Ti—V—Al based alloy of the present invention exhibits superelasticity throughout a broad range of temperatures from about 80° C. to about liquid nitrogen temperature. Therefore, the alloy of the present invention is useful as a material for various controlling device elements that are operated within such a broad range of temperatures.

(2) Further, the Ti—V—Al based alloy of the present invention is useful as an aircraft material owing to its excellence in corrosion resistance, low temperature plastic workability and lightness.

(3) Moreover, since the Ti—V—Al based alloy of the present invention is neither carcinogenic nor allergenic and does not substantially affect the body, the alloy is usable as a medical material, an accessory material, an eyeglass frame material, etc.

EXAMPLES

Figure 1:
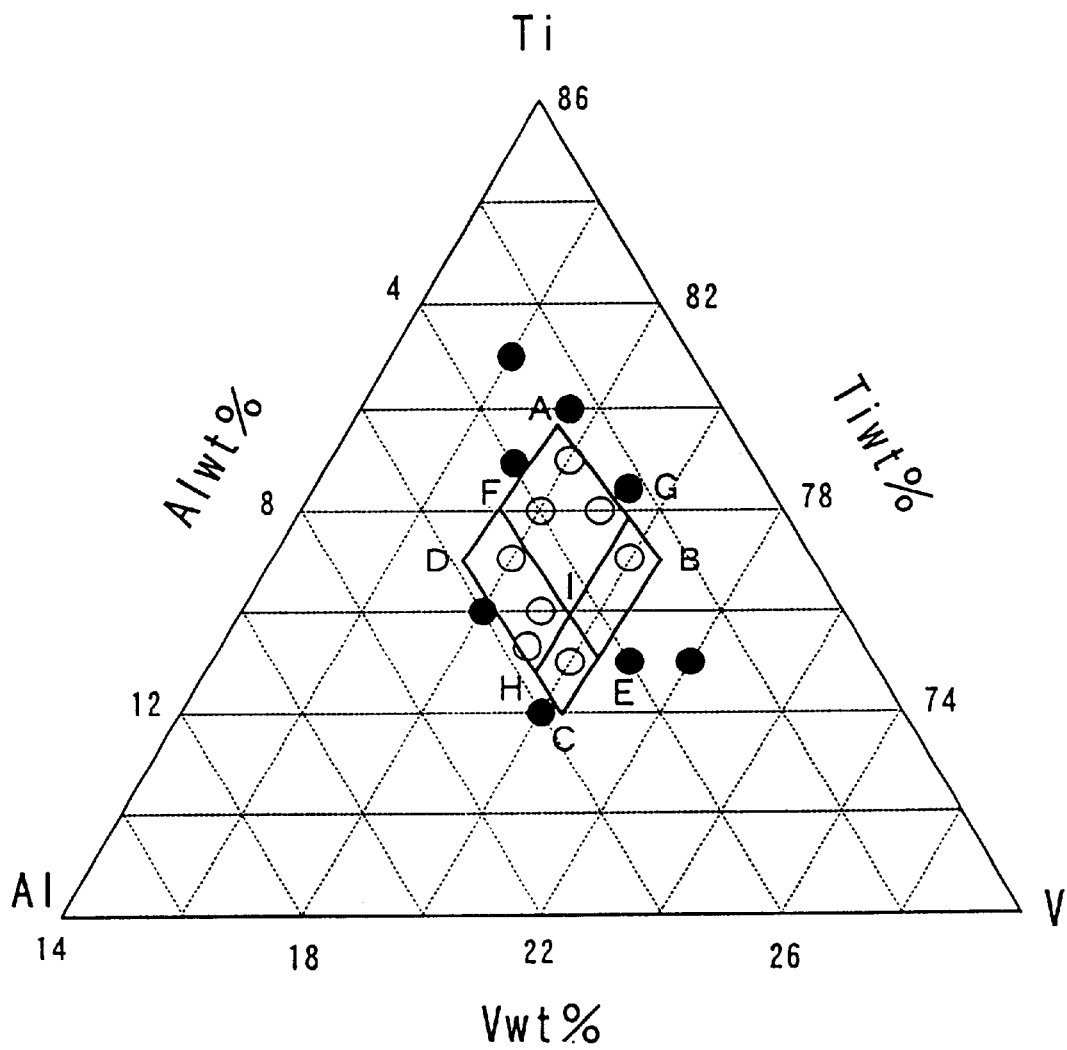
FIG. 1 is a diagram showing the tertiary composition range of the Ti—V—Al based alloy according to the present invention.

The following examples are provided to further illustrate the features of the invention. It is to be understood that the examples are illustrative only and are not intended in any way to limit the scope of the invention.

Examples 1–8 and Comparative Examples 1–8

Commercially available pure titanium, pure aluminum and pure vanadium were weighed and mixed in the proportions (wt. %) shown in Table 1 (so as to prepare about 30 g of test button-shaped alloy ingots). The basic metal mixture was placed in a copper melting pot with water-cooling, and arc-melted in an argon atmosphere using a non-consumable tungsten electrode, thereby producing an alloy.

The ingot obtained was held under vacuum conditions at 1100° C. for 24 hours for heat treatment and immersed in water at temperatures no higher than 10° C., thereby quenching at a rate of at least 600° C./sec. Subsequently, the quenched ingot was rolled to a thickness of 0.5 to 1 mm and cut into strips about 5 to 8 mm wide, followed by annealing under vacuum conditions at 850° C. for 1 hour. Sixteen kinds of samples of alloys of Examples 1–8 and Comparative Example 1–8 were prepared in this manner. Table 1 shows the compositions and properties of the samples.

In the above process, the samples were rolled to a draft of at least 90% and evaluated for their cold workability according to the following criteria:

A: cracking did not occur;
B: cracking occurred during cold rolling.

Vickers hardness of the samples after the annealing step to relieve strain was measured using a microhardness meter.

Further, the samples after the annealing step to relieve strain were pressed against a cylindrical bar about 10 mm in diameter at room temperature. In this state, a bending force was applied until the samples were bent at about 90 degrees to form an L shape. After removal of the bending force, the samples were tested for their shape restorability. The shape restorability was determined by measuring the space, if any, between the horizontal plane and the point of the sample 30 mm away from the point originally deformed by the bending force. Evaluation was made according to the following criteria:

A: 0 mm in space (complete recovery from strain)
B: less than 10 mm in space (satisfactory recovery from strain)
C: 10 mm or more in space (poor recovery from strain)

TABLE 1

| | Composition (wt. %) | | | Cold workability | Vickers hardness | Shape restorability |
|---|---|---|---|---|---|---|
| | Ti | V | Al | | | |
| Ex. 1 | 79.0 | 18.0 | 3.0 | A | 268 | A |
| Ex. 2 | 78.0 | 19.0 | 3.0 | A | 216 | A |
| Ex. 3 | 77.0 | 20.0 | 3.0 | A | 205 | B |
| Ex. 4 | 78.0 | 18.0 | 4.0 | A | 263 | A |
| Ex. 5 | 77.0 | 18.0 | 5.0 | A | 258 | A |
| Ex. 6 | 76.0 | 19.0 | 5.0 | A | 228 | A |
| Ex. 7 | 75.0 | 20.0 | 5.0 | A | 252 | B |
| Ex. 8 | 75.5 | 19.0 | 5.5 | A | 217 | B |
| Comp. Ex. 1 | 78.0 | 19.5 | 2.5 | A | 289 | C |
| Comp. Ex. 2 | 80.0 | 17.5 | 2.5 | A | 285 | C |
| Comp. Ex. 3 | 81.0 | 16.0 | 3.0 | A | 315 | C |
| Comp. Ex. 4 | 75.0 | 22.0 | 3.0 | A | 275 | C |
| Comp. Ex. 5 | 79.0 | 17.0 | 4.0 | A | 318 | C |
| Comp. Ex. 6 | 75.0 | 21.0 | 4.0 | A | 269 | C |
| Comp. Ex. 7 | 76.0 | 18.0 | 6.0 | B | 295 | C |
| Comp. Ex. 8 | 74.0 | 20.0 | 6.0 | B | 384 | Broken |

As is clear from Table 1, Ti—V—Al alloys of Examples 1–8 and Comparative Examples 1–6 have good cold workability. By contrast, Ti—V—Al alloys of Comparative Examples 7 and 8 containing more than 6% aluminum have poor cold workability.

The Ti—V—Al alloys of Examples 1–8 generally have low hardness and good cold workability. By contrast, the alloys of Comparative Examples 1–8 generally have high hardness and poor cold workability.

Furthermore, the Ti—V—Al alloys of Examples 1–8 have excellent shape restorability. Particularly, the alloys of Examples 1, 2, 4 to 6 were completely restored. By contrast, the alloys of Comparative Examples were not fully restored. Particularly, the alloy of Comparative Example 8 was broken when a force was applied.

The results of Table 1 clearly show that the Ti—V—Al alloys according to the present invention are highly suitable for practical use.

Test Example 1

Sixteen kinds of annealed alloy samples of Examples 1–8 and Comparative Example 1–8 were tested for their superelaticity by the following method. The samples were bent at about 200° C. until a surface maximum strain of about 2.5% was attained.

The alloy samples of Examples 1–8 whose compositions fall within the range defined by the points of A, B, C and D in FIG. 1 exhibited superelastic properties, i.e., "almost perfect superelasticity" or "partial superelasticity".

Test Example 2

Plate-shaped alloy samples of Example 2 were bent in boiling water in a similar manner as in Test Example 1. The samples exhibited partial superelasticity.

Test Example 3

Plate-shaped alloy samples of Example 2 were subjected to a low temperature aging treatment at about room temperature (temperature at which ω phase does not form) for about 7000 hours. The samples were deformed at different temperatures to a strain of at least about 2%, followed by removing the deforming load. FIGS. 2–5 are graphs showing stress-strain curves of the samples at various temperatures.

Figure 2:
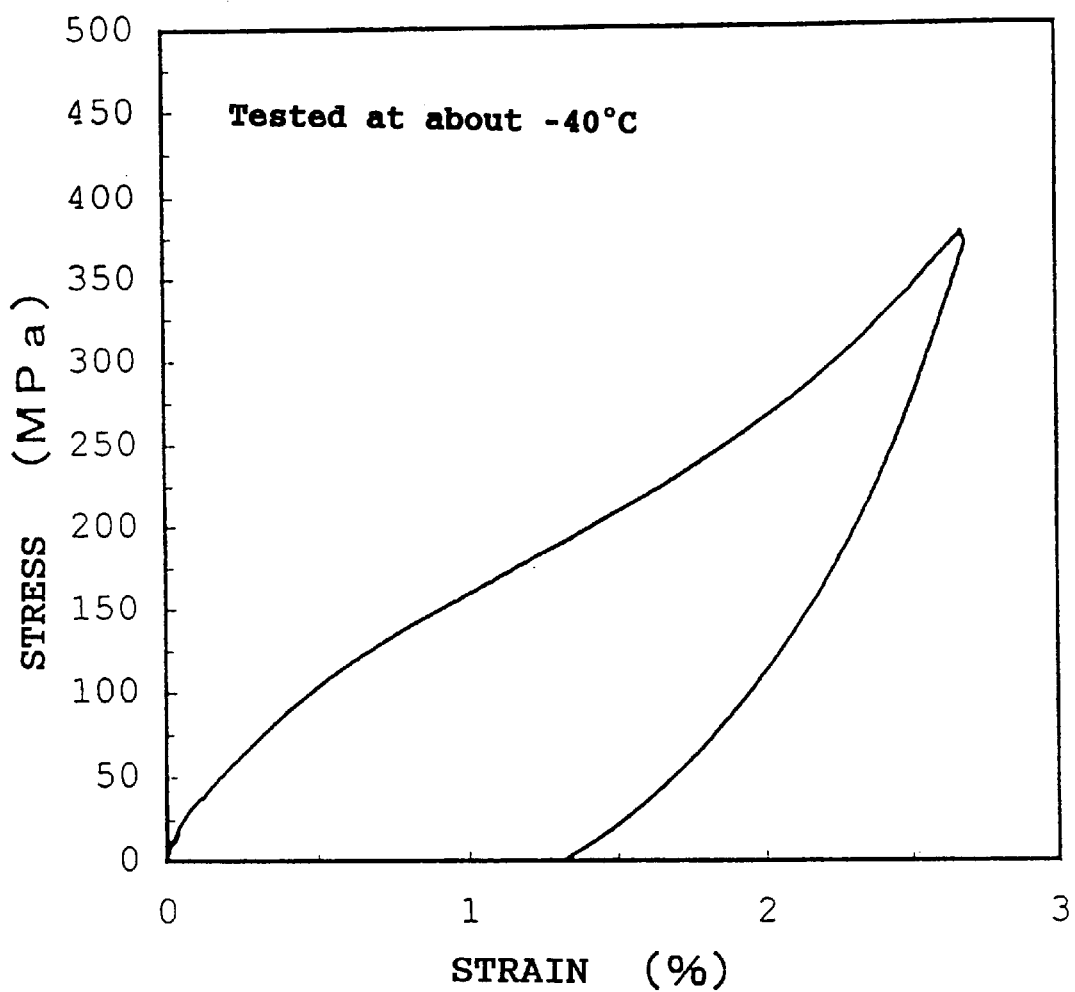
FIG. 2 is a graph of strain-stress curves at about −40° C. of a Ti—V—Al based alloy according to an embodiment of the present invention.
Figure 3:
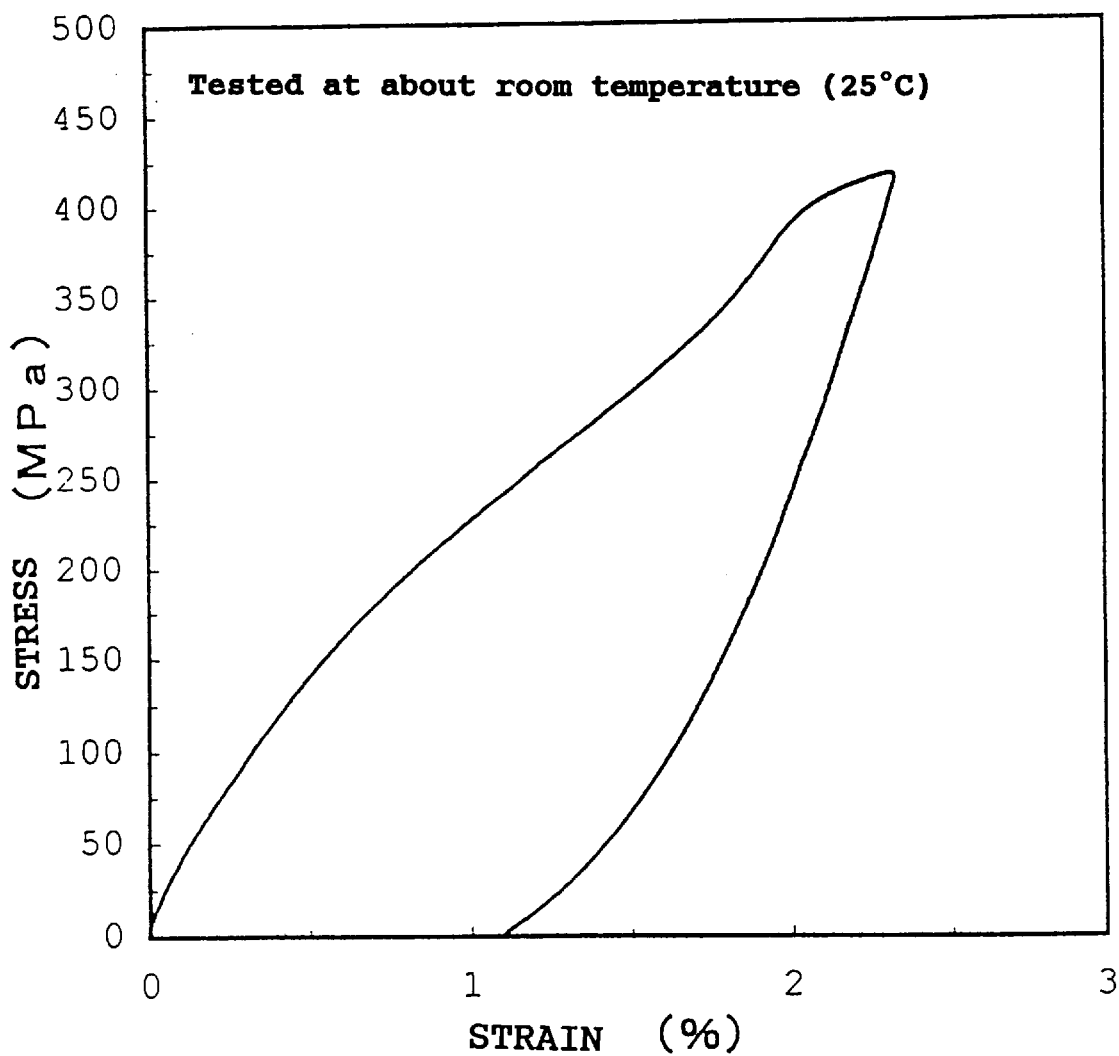
FIG. 3 is a graph of stress-strain curves at room temperature of the Ti—V—Al based alloy according to the embodiment of the present invention.
Figure 4:
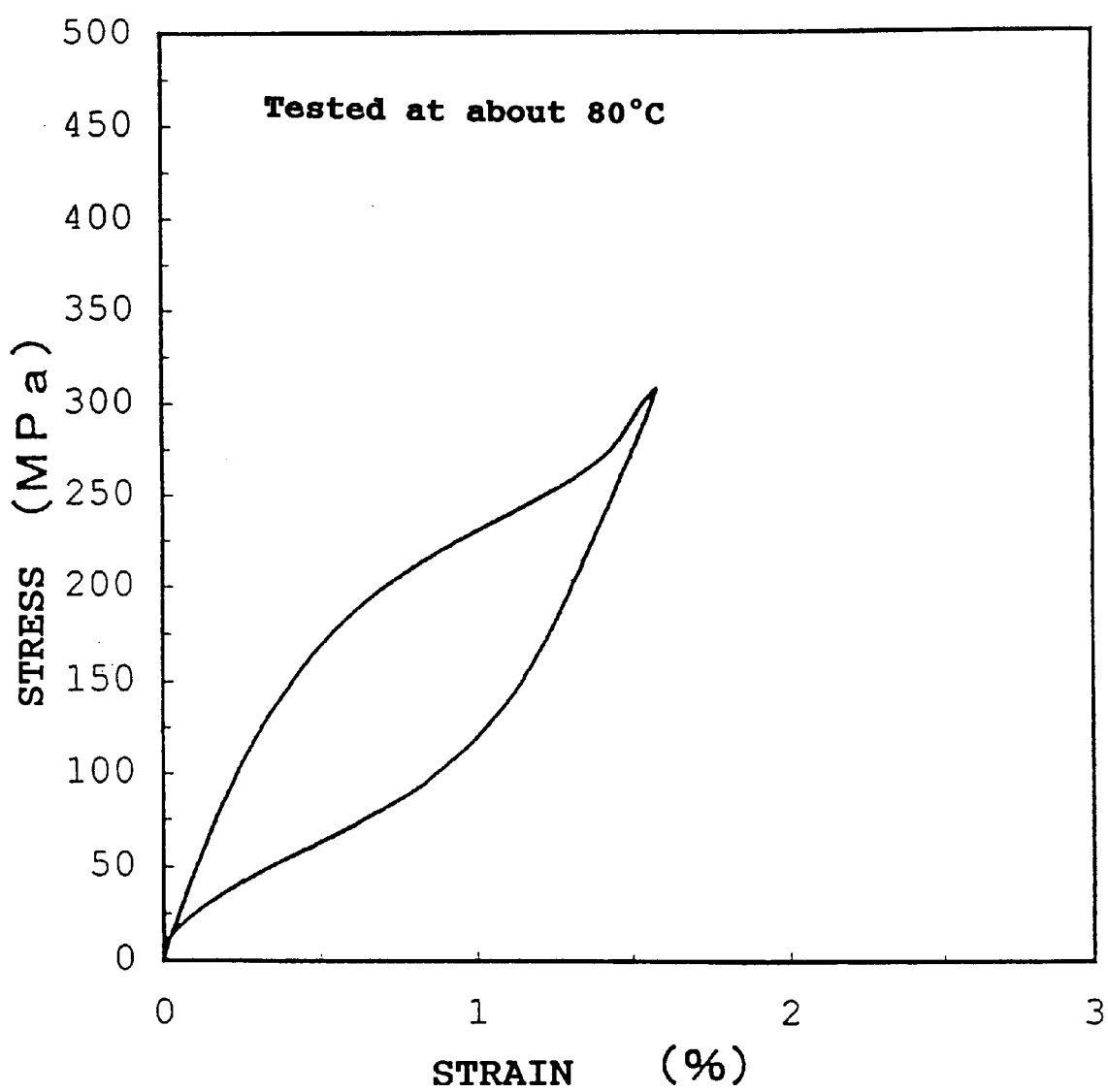
FIG. 4 is a graph of stress-strain curves at about 80° C. of the Ti—V—Al based alloy according to the embodiment of the present invention.
Figure 5:
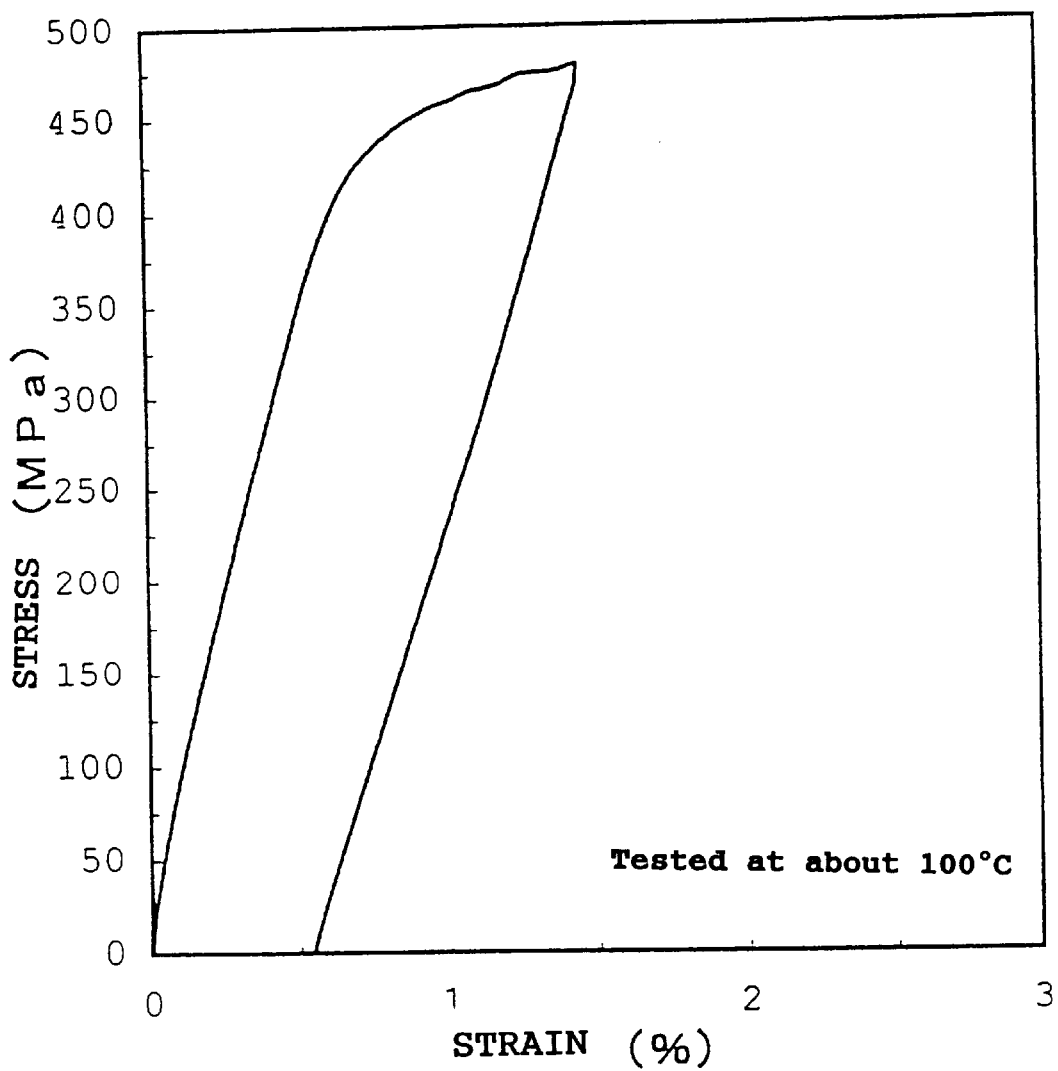
FIG. 5 is a graph of stress-strain curves at about 100° C. of the Ti—V—Al based alloy according to the embodiment of the present invention.

As shown in FIGS. 2, 3 and 4, the alloy of Example 2 exhibited superelasticity throughout a broad range of temperatures ranging from −40° C., about room temperature to 80° C. The alloy, however, did not exhibit superelasticity at about 100° C., as shown in FIG. 5. In FIG. 5, strain decreases linearly. This means that the strain was relieved only in the area deformed elastically.

When plate-shaped alloy samples of Example 2 were aged at 100° C. (temperature at which ω phase does not form) for about 235 hours, similar results were obtained.

Of the conventional Ti—V—Al based alloys, there are no known functional alloys that exhibit superelasticity throughout such a broad range of temperatures. Such functional alloys are obtained by the present invention for the first time.

Test Example 4

Plate-shaped alloy samples of Example 2 were subjected a low temperature aging treatment at room temperature for about 7000 hours. About 1% of strain was given to the samples under a deforming load at room temperature or at liquid nitrogen temperature (−196° C.), thereby bending the samples to form an L shape. Upon removal of the load at the same temperatures, the samples were restored almost to their original configurations due to superelasticity.

Of the conventional Ti—V—Al based alloys, there are no known functional alloys that exhibit superelasticity throughout such a broad range of temperatures. Such functional alloys are obtained by the present invention for the first time.

Test Example 5

Plate-shaped alloy samples of Example 2 were aged at room temperature for about 7000 hours. The samples were deformed at liquid nitrogen temperature in such a way that some degree of deformation was left. As the temperature was raised gradually, the samples were restored almost to their original shapes at temperatures ranging from −50° C. to 20° C.

Upon comparison of the results between Test Example 2 and Test Example 5, it is estimated that the low temperature aging treatment decreases the phase transformation temperature of the alloy of the present invention.

Test Example 6

Plate-shaped alloy samples of Example 2 were aged at 100° C. or 150° C. for 235 hours. The samples were deformed at liquid nitrogen temperature in such a way that some degree of deformation was left. As the temperature was raised gradually, the samples were restored almost to their original shapes at 20° C.

In contrast to the above, when aged at 200° C. for 50 hours, the samples had increased hardness presumably due to the ω phase formation, and did not exhibit superelasticity.

What is claimed is:

1. A Ti—V—Al based superelastic alloy wherein the proportions of Ti, Al and V, based on the total weight of the three components, fall within the range defined by the lines joining the following points of A, B, C and D shown in the ternary composition diagram of accompanying FIG. 1:

A: 79.8% Ti, 17.5% V, 2.7% Al,
B: 76.8% Ti, 20.5% V, 2.7% Al,

C: 73.8% Ti, 20.5% V, 5.7% Al,

D: 76.8% Ti, 17.5% V, 5.7% Al.

2. A process for preparing a Ti—V—Al based superelastic alloy, which comprises forming an alloy wherein the proportions of Ti, Al and V, based on the total weight of the three components, fall within the range defined by the lines joining the following points of A, B, C and D shown in the ternary composition diagram of accompanying FIG. 1, followed by heat treatment at 800° C. to 1200° C. and quenching:

A: 79.8% Ti, 17.5% V, 2.7% Al,

B: 76.8% Ti, 20.5% V, 2.7% Al,

C: 73.8% Ti, 20.5% V, 5.7% Al,

D: 76.8% Ti, 17.5% V, 5.7% Al.

3. A process for preparing a Ti—V—Al based superelastic alloy, which comprises forming an alloy wherein the proportions of Ti, Al and V, based on the total weight of the three components, fall within the range defined by the lines joining the following points of A, B, C and D shown in the ternary composition diagram of accompanying FIG. 1, followed by heat treatment at 800° C. to 1200° C. and quenching and then aging the alloy at temperatures no higher than 200° C.:

A: 79.8% Ti, 17.5% V, 2.7% Al,

B: 76.8% Ti, 20.5% V, 2.7% Al,

C: 73.8% Ti, 20.5% V, 5.7% Al,

D: 76.8% Ti, 17.5% V, 5.7% Al.

4. The Ti—V—Al alloy produced from the process according to claim 2.

5. The Ti—V—Al alloy produced from the process according to claim 1.

* * * * *